(12) United States Patent
Majeed et al.

(10) Patent No.: US 9,539,232 B1
(45) Date of Patent: Jan. 10, 2017

(54) CALEBIN A FOR OSTEOPOROSIS

(71) Applicants: Muhammed Majeed, Edison, NJ (US); Kalyanam Nagabhushanam, East Windsor, NJ (US)

(72) Inventors: Muhammed Majeed, Edison, NJ (US); Kalyanam Nagabhushanam, East Windsor, NJ (US)

(*) Notice: Subject to any disclaimer, the term of this patent is extended or adjusted under 35 U.S.C. 154(b) by 0 days.

(21) Appl. No.: 15/228,142

(22) Filed: Aug. 4, 2016

(51) Int. Cl.
*A61K 31/215* (2006.01)
*A61K 31/216* (2006.01)
*A61K 8/67* (2006.01)

(52) U.S. Cl.
CPC ............. *A61K 31/216* (2013.01); *A61K 8/671* (2013.01)

(58) Field of Classification Search
CPC ...................................... A61K 8/671
USPC ......................................... 514/529
See application file for complete search history.

(56) References Cited

U.S. PATENT DOCUMENTS

| | | | | |
|---|---|---|---|---|
| 9,328,330 B2 * | 5/2016 | Majeed | ................ | C12N 5/0653 |
| 2015/0196524 A1 * | 7/2015 | Majeed | ................ | A61K 31/235 514/543 |
| 2015/0306060 A1 * | 10/2015 | Majeed | .................. | A61K 31/25 514/543 |
| 2016/0199340 A1 * | 7/2016 | Nagabhushanam | . | A61K 31/235 514/543 |

* cited by examiner

*Primary Examiner* — Raymond Henley, III (57) ABSTRACT

Disclosed is the therapeutic potential of Calebin A for osteoporosis (bone loss) caused by aging or chronic disease conditions like cancer. Calebin A is shown to down modulate osteoclastogenesis induced by receptor activator of nuclear factor (NF)-κB ligand (RANKL) signalling thereby having therapeutic potential for osteoporosis.

5 Claims, 13 Drawing Sheets

Fig. 1a

Calebin A

CALEBIN A FOR OSTEOPOROSIS

BACKGROUND OF THE INVENTION

Field of the Invention

The invention in general pertains to osteoporosis and therapeutic interventions thereof in mammals. More specifically, the present invention pertains to the therapeutic potential of Calebin A for osteoporosis wherein calebin A in therapeutically effective amounts is shown to inhibit mammalian osteoclastogenesis by the suppression of the RANKL signaling pathway thereby evincing therapeutic potential for osteoporosis.

Description of the Prior Art

An estimated 61 million people aged 50 years or older in the United States would be prone to risk for fractures following osteoclast related bone diseases like osteoporosis or low bone mass by 2020 due to the non availability of widely implemented and effective treatment. According to the American Academy of Orthopedic Surgeons, the projected cost of osteoporosis care over the next 2 decades will be approximately $474 billion (Z. Jin, X. Li, Y. Wan, Mol. Endocrinol. 29 (2015) 172-186).

Bone metastasis is common sequelae of multiple myeloma or advanced breast, prostate, lung, colon, kidney, thyroid, and stomach carcinomas (R. E. Coleman, Cancer Treat. Rev. 27 (2001) 165-176 and R. E. Coleman, Clin. Cancer Res. Off. J. Am. Assoc). The involvement of a cytokine belonging to the tumour necrosis factor (TNF) family called receptor activator of nuclear factor (NF)-κB ligand (RANKL) in such metastasis has been reported in the art (T. Onishi, N. Hayashi, R. L. Theriault, G. N. Hortobagyi, N. T. Ueno, Nat. Rev. Clin. Oncol. 7 (2010) 641-651). RANKL has been demonstrated to possess osteoclastogenic activity, whereby RANKL directs the differentiation of bone monocytes to osteoclasts which promote bone resorption (D. L. Lacey, E. Timms, H. L. Tan, M. J. Kelley, C. R. Dunstan, T. Burgess, R. Elliott, A. Colombero, G. Elliott, S. Scully, H. Hsu, J. Sullivan, N. Hawkins, E. Davy, C. Capparelli, A. Eli, Y. X. Qian, S. Kaufman, I. Sarosi, V. Shalhoub, G. Senaldi, J. Guo, J. Delaney, W. J. Boyle, Cell 93 (1998) 165-176 and S. L. Teitelbaum, Science 289 (2000) 1504-1508).

Curcumin is also reported to suppress osteoclastogenesis (A. C. Bharti, Y. Takada, B. B. Aggarwal, J. Immunol. (2004) 172, 5940-5947). Other natural ingredients for managing osteoporosis and cancer induced osteoclastogenesis remain to be investigated. Calebin A as a natural ingredient is known in the art for its anti-cancer properties (Li Y et al, "Calebin-A induces apoptosis and modulates MAPK family activity in drug resistant human gastric cancer cells", Eur J Pharmacol. 2008 Sep. 4; 591(1-3):252-258 and Aggarwal B B et al, "Curcumin-free turmeric exhibits anti-inflammatory and anticancer activities: Identification of novel components of turmeric", Mol Nutr Food Res. 2013 September; 57(9): 1529-42). The present invention investigates the ability of calebin A to suppress osteoclastogenesis in mammals.

It is the principle objective of the invention to disclose the therapeutic potential of calebin A for mammalian osteoporosis wherein calebin A is shown to inhibit both RANKL- and cancer-induced osteoclastogenesis.

The present invention fulfils the aforesaid objective and also provides related advantages.

SUMMARY OF THE INVENTION

The present invention discloses the therapeutic potential of Calebin A for osteoporosis (bone loss) caused by aging or chronic disease conditions like cancer. Calebin A is shown to down modulate osteoclastogenesis induced by receptor activator of nuclear factor (NF)-κB ligand (RANKL) signalling thereby having therapeutic potential for osteoporosis.

Other features and advantages of the present invention will become apparent from the following more detailed description, taken in conjunction with the accompanying images, which illustrate, by way of example, the principle of the invention.

DETAILED DESCRIPTION OF THE MOST PREFERRED EMBODIMENTS

FIGS. 1b, 1c, 1d, 2a, 2b, 2c, 3a, 3b, 3c, 4a, 4b, 4c, 5a, 5b, 5c, 5d, 5e, 6a, 6b, 6c, 6d, 7a, 7b

In the most preferred embodiments, the present invention relates to the following.

A method of inhibiting osteoclastogenesis in mammals, said method comprising steps of bringing into contact mammalian osteoclast progenitor cells with an effective concentration of calebin A to bring about effect of inhibiting differentiation of said progenitor cells into osteoclasts. In a preferred embodiment, said progenitor cell is macrophage.

A method of inhibiting gene and protein expression associated with up-regulation of osteoclastogenesis in mammals said method comprising steps of bringing into contact mammalian osteoclast progenitor cells with an effective concentration of calebin A to bring about down-regulation of said gene and protein expression in the mammalian progenitor cells.

Calebin A for use in therapeutic management of osteoporosis in mammals wherein osteoporosis results from osteoclastogenesis in said mammals.

Compositions comprising calebin A for use in therapeutic management of osteoporosis in mammals wherein osteoporosis results from osteoclastogenesis in said mammals.

A method of therapeutic management of osteoporosis induced by osteoclastogenesis in mammals, said method comprising step of administering therapeutically effective amounts of calebin A to mammals in need of said therapeutic management to bring about the effect of osteoclastogenesis inhibition.

A method of therapeutically managing mammalian osteoporosis resulting from cancer induced differentiation of osteoclast progenitor cells into osteoclasts, said method comprising step of bringing into contact effective concentration of calebin A, said progenitor cells and said cancer cells to bring about the effect of osteoclastogenesis inhibition.

The specific examples included herein below illustrate the most preferred embodiments of the present invention.

EXAMPLES

Example 1

Materials and Methods

Reagents

A 50-mM solution of calebin A (Sabina Corporation, NJ, USA) in dimethyl sulfoxide was prepared and stored in small aliquots at −20° C. It was appropriately diluted in the culture medium before use. Dulbecco modified Eagle's medium (DMEM), DMEM/F-12, RPMI 1640, fetal bovine serum (FBS), an antibiotic-antimycotic mixture, and 0.4% trypan blue vital stain were procured from Mediatech, Inc. (Manassas, Va.). Recombinant RANKL protein was provided by Dr. Bryant Darnay of The University of Texas MD Anderson Cancer Center (Houston, Tex.). Antibodies against Iκκα, Iκκβ, and IκBα were purchased from Imgenex (San Diego, Calif.). Antibodies against phospho-IκBα (Ser32/36), cFms, TRAP, Cathepsin K and Calcitonin R were purchased from Cell Signalling Technology (Danvers, Mass.). Antibodies against RANK, extracellular signal-related kinase 2 (ERK2) and phospho-ERK1/2 (Thr202/Tyr204) were obtained from Santa Cruz Biotechnology (Santa Cruz, Calif.). NFATc1 antibody was obtained from Addgene (Cambridge, Mass., USA), M-CSF was from R&D Systems (Minneapolis, Minn., USA). Goat anti-rabbit and goat anti-mouse horseradish peroxidase conjugates were purchased from Bio-Rad (Hercules, Calif.). β-actin antibody and a leukocyte acid phosphatase kit (387-A) for tartrate-resistant acid phosphatase (TRAP) staining were purchased from Sigma-Aldrich (St. Louis, Mo.). The cell-permeable NFκB essential modulator (NEMO: also called Iκκg)-binding domain peptide (NBP) was purchased from Imgenex. [g-32P]ATP was purchased from MP Biomedicals (Solon, Ohio).

Cell Lines

RAW264.7 mouse macrophage cells were received from by Dr. Bryant Darnay. The cells were cultured in DMEM/F-12 supplemented with 10% FBS and antibiotics. The RAW 264.7 cell line has been shown to express RANK and differentiates into functional TRAP-positive osteoclasts when cultured with soluble RANKL. Moreover, RANKL has also been shown to activate NFκB in RAW264.7 cells. MDA-MB-231 (human breast adenocarcinoma) and U266 (human muhiplemyeloma) cells were obtained from the American Type Culture Collection (Manassas, Va.). The MDA-MB-231 cells were cultured in DMEM and the U266 cells in RPMI 1640 with 10% FBS.

Osteoclast Differentiation Assay

To determine the effects of calebin A on RANKL-induced osteoclast differentiation, the RAW264.7 cells were cultured at a density of $5 \times 10^3$ cells per well in 24-well plates and allowed to adhere overnight. The medium was then replaced and the cells were treated with 5 nM RANKL for 5 days. After the incubation, the cells were subjected to TRAP staining using leukocyte acid phosphatase kit. For co-culture experiments with cancer cells, RAW 264.7 cells were seeded at a density of $5 \times 10^3$ cells per well and allowed to adhere overnight. U266 or MDA-MB-231 cells, at a density of $1 \times 10^3$ cells per well, were added to the RAW 264.7 cells the following day. The wells were treated with calebin A, and co-cultured for 5 days before being subjected to TRAP staining. For conditioned medium experiments, RAW 264.7 cells were seeded at a density of $5 \times 10^3$ cells per well and allowed to adhere overnight. The following day, the medium was replaced with ⅘ of RAW 264.7 medium (DMEM/F12) plus ⅕ of conditioned medium from MDA-MB-231 or U266 cells. For that procedure, the supernatant of cultured cancer cells that had been centrifuged was used. Finally, the RAW264.7 cells were cultured for 5 days and subjected to TRAP staining and an electrophoretic mobility shift assay (EMSA).

Cell Proliferation Assay

The effects of calebin A on the proliferation of RAW 264.7 cells were determined by measuring mitochondrial dehydrogenase activity with 3-[4,5-dimethylthiazol-2-yl]-2,5-diphenyl tetrazolium bromide (MTT) as the substrate as described in B. Sung, S. Prasad, V. R. Yadav, S. C. Gupta, S. Reuter, N. Yamamoto, A. Murakami, B. B. Aggarwal, PloS One 8 (2013) e64118. In brief, 3000 RAW264.7 cells (in 0.1 ml media) per well were incubated with various concentrations of calebin A, in triplicate, in 96-well plates at 37° C. for 1, 3, or 5 days. At each interval, MTT solution was added to each well, and the plates were incubated for 2 h at 37° C. An extraction buffer (100 mM) comprised of 20% sodium dodecyl sulphate (SDS) and 50% dimethyl formamide was added, and the cells were incubated overnight at 37° C. to dissolve the formazan formed during the reaction. The absorbance of the coloured product was then measured at 570 nm using a 96-well multiscanner (MRX Revelation, Dynex Technologies, Chantilly, Va.).

Western Blot Analysis

To determine protein expression levels, the cytoplasmic and whole cell extracts were prepared and were fractionated using 10% sodium dodecyl sulphate polyacrylamide gel electrophoresis (SDSPAGE). After electrophoresis, the proteins were transferred to nitrocellulose membranes, blotted with the relevant antibodies, and detected with enhanced chemiluminescence reagent (GE Healthcare, Piscataway, N.J.).

Electrophoretic Mobility Shift Assay for NFκB

To assess NFκB activation in the nuclear extracts, EMSA was carried out using the procedure described by Y. Li, S. Li, Y. Han, J. Liu, J. Zhang, F. Li, Y. Wang, X. Liu, L. Yao, Eur. J. Pharmacol. 591 (2008) 252-258. In brief, nuclear extracts from untreated and RANKL-treated RAW 264.7 cells were incubated with the 32P-end-labeled 45-mer double-stranded NFκB oligonucleotide (15 mg protein with 16 fM DNA) from the HIV long terminal repeat, 5'-TTGTTA-CAAGGGACTTTCCGCTGGGGACTTTCCA-GGGGGAGGCGTGG-3'(boldface indicates NFκB binding sites), for 30 min at 37° C. The DNA-protein complex formed was separated from free oligonucleotides on 6.6% native polyacrylamide gels. The dried gels were visualized with a Storm 820 molecular imager (Amersham, Piscataway, N.J., USA), and radioactive bands were quantified using a densitometer and Image Quant software (ImageJ software, NIH, USA).

Transfection of p65 Plasmid

To determine the role of NF-κB/p65 expression on calebin A-induced inhibition osteoclastogenesis, RAW 264.7 cells ($5 \times 10^5$ cells/well) were plated in 6-well plates and transiently transfected by the calcium phosphate method with pNF-κB (0.5 mg) and control plasmid pCMVFLAG1 DNA for 24 h. The medium was then replaced, and the cells were treated with RANKL (5 nM) and or calebin A (5 mM) for 5 days. All cells were subjected to TRAP staining using the leukocyte acid phosphatase kit.

Statistical Analysis

Data were analysed using ImageJ software (NIH, USA) and are presented as mean±standard deviation (SD). The statistical significance of differences was assessed by student t-test. P values<0.05 were considered statistically significant.

Example 2

Results

Calebin A Inhibits RANKL-Induced Osteoclastogenesis

Figure 1A:
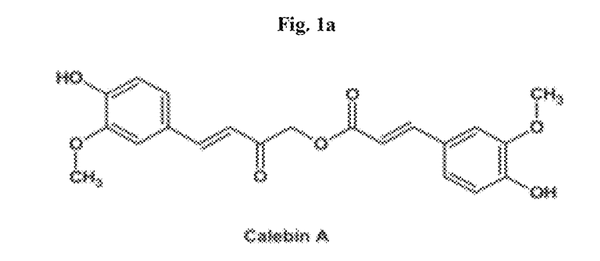
FIG. 1a shows the structure of Calebin A.
Figure 1B:
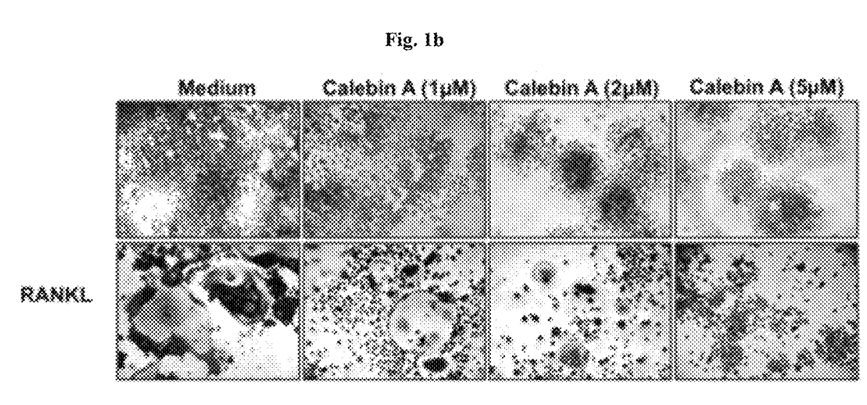
FIG. 1b shows the TRAP (Tartrate-resistant acid phosphatase) expression (TRAP positive cells) in RAW264.7 mouse macrophage cells ($5 \times 10^3$ cells/mL) stained to show osteoclastogenesis. The cells were incubated with RANKL (5 nM), or RANKL plus calebin A of concentrations 0, 1, 2, 5 mM for 5 days. Original magnification—100×.
Figure 1C:
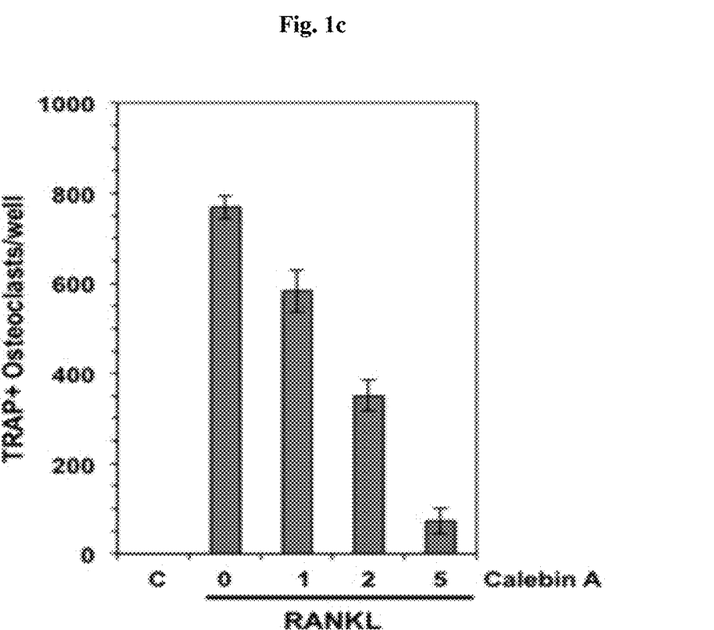
FIG. 1c shows the quantification of multinucleated osteoclasts (≥3 or more nuclei) after treatment with RANKL (5 nM) alone or RANKL plus calebin A of concentrations 0, 1, 2, 5 mM for 5 days. The values are expressed as mean of 3 measurements±standard deviation (SD).
Figure 1D:
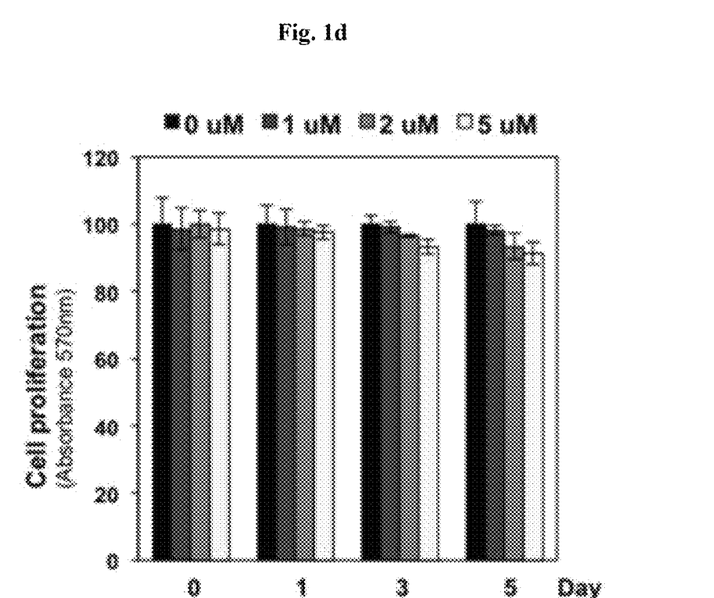
FIG. 1d shows the proliferation of mouse macrophage cells, as assessed by the MTT method. RAW 264.7 cells ($3 \times 10^3$ cells per 100 ml) were incubated with medium only (Control) or with 1, 2, or 5 mM concentrations of calebin A for 1, 3 and 5 days.

To validate the RANKL-induced osteoclastogenesis inhibition potential of calebin A, RAW 264.7 cells were treated with different concentrations of calebin A in the presence of RANKL. The cells were then allowed to differentiate into osteoclasts. The morphological features of the cells were observed which clearly revealed the differentiation of cells into osteoclasts (FIG. 1b). However, with exposure to increasing concentrations of calebin A, decreased in the RANKL-induced osteoclast formation was observed, as measured by counting the number of TRAP-positive osteoclasts per well (FIG. 1c). Cell proliferation was assessed at the same concentrations of calebin A at days 1, 3, and 5. Calebin A treatment did not significantly affect the proliferation of RAW 264.7 cells, excluding the possibility that the observed decrease in TRAP-positive osteoclasts was attributable to a reduction in cell proliferation by calebin A treatment (FIG. 1d).

Figure 2A:
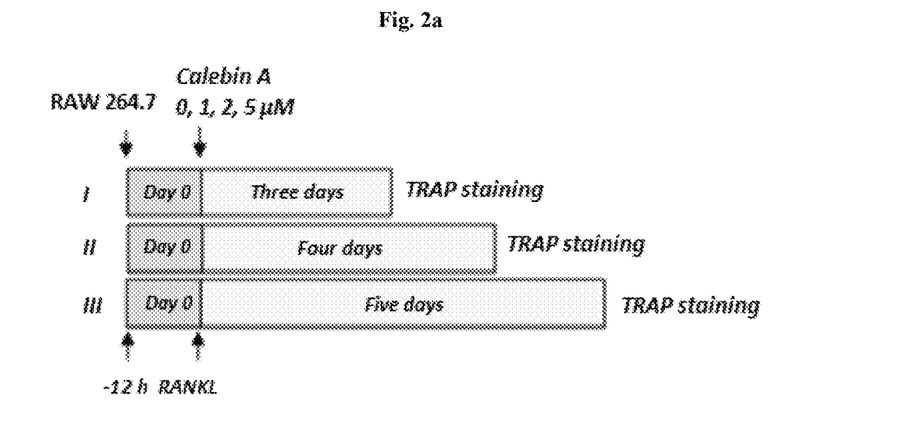
FIG. 2a shows the schematic representation of treatment schedule to validate the inhibition of RANKL-induced osteoclastogenesis by calebin A.
Figure 2B:
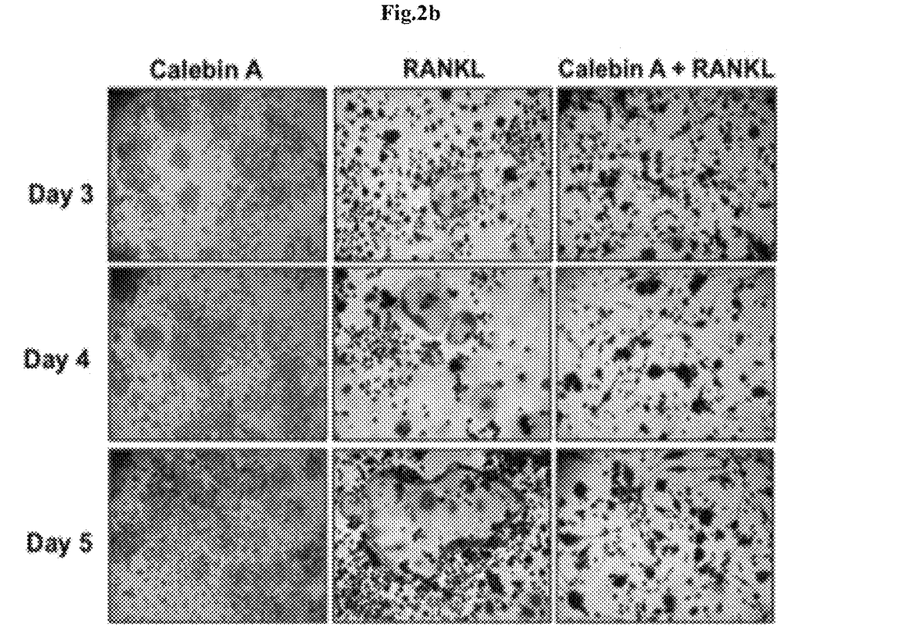
FIG. 2b shows the TRAP expression in stained mouse macrophage cells—RAW264.7 ($5 \times 10^3$ cells/mL) incubated with 5 nM RANKL, 5 mM calebin A, or both for 3, 4 and 5 days. Original magnification—100×.
Figure 2C:
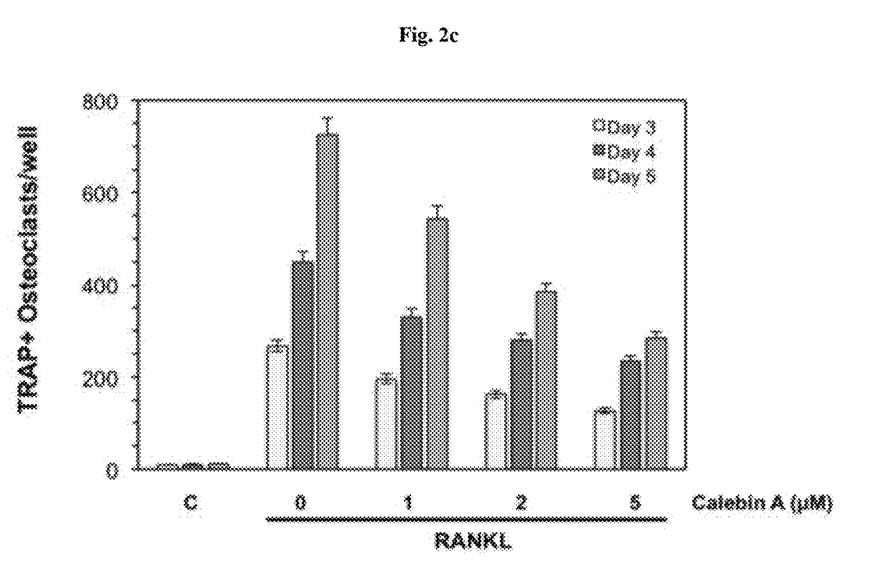
FIG. 2c shows the multinucleated osteoclast (≥3 nuclei) count of RAW 264.7 ($5 \times 10^3$ cells/mL) incubated with either medium (C) or RANKL (5 nM) along with the indicated concentrations of calebin A for 3, 4, and 5 days, stained to show TRAP expression. The values are mean of 3 measurements±SD.

To determine whether calebin A's inhibitory effect on osteoclastogenesis was time-dependent, RAW 264.7 cells were treated with RANKL and calebin A and incubated for 3, 4, or 5 days to differentiate into osteoclasts (FIG. 2a). Morphological observation revealed that RAW 264.7 cells treated with RANKL differentiated into osteoclasts and this differentiation was inhibited by the addition of calebin A (FIG. 2b). Moreover, RANKL induced osteoclast differentiation was observed to be time dependent, with the maximum number of TRAP-positive osteoclasts per well reached at day 5 (FIG. 2b). However, calebin A decreased the number of TRAP-positive osteoclasts in a dose-dependent manner, with the strongest inhibition at a dose of 5 mM at all time points (FIG. 2c).

Calebin A Acts at an Early Step in the RANKL-Induced Osteoclastogenesis Pathway

Figure 3A:
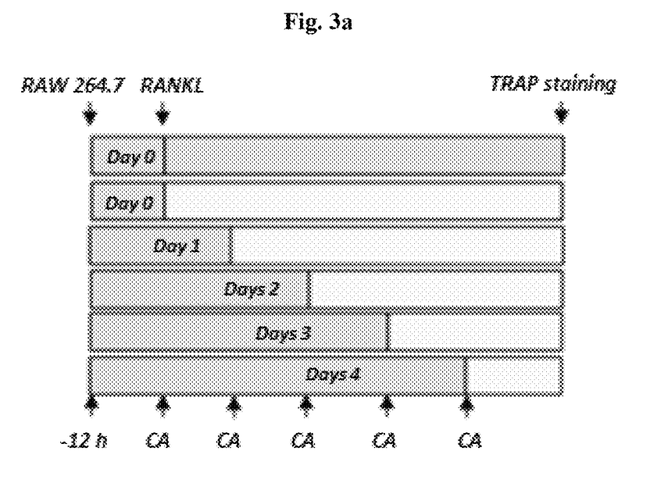
FIG. 3a shows the schematic representation of the treatment schedule to show the inhibition of RANKL-induced osteoclastogenesis by calebin A, 24 h after stimulation.
Figure 3B:
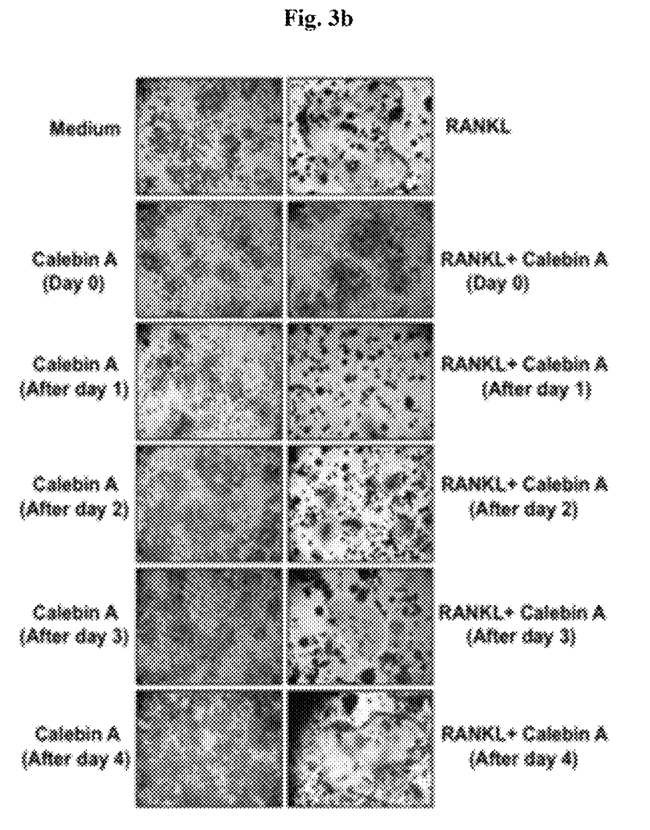
FIG. 3b shows the TRAP expression in day 5—stained RAW264.7 cells ($5 \times 10^3$ cells/mL), incubated with medium, RANKL (5 nM), calebin A (5 mM) or RANKL and calebin A.
Figure 3C:
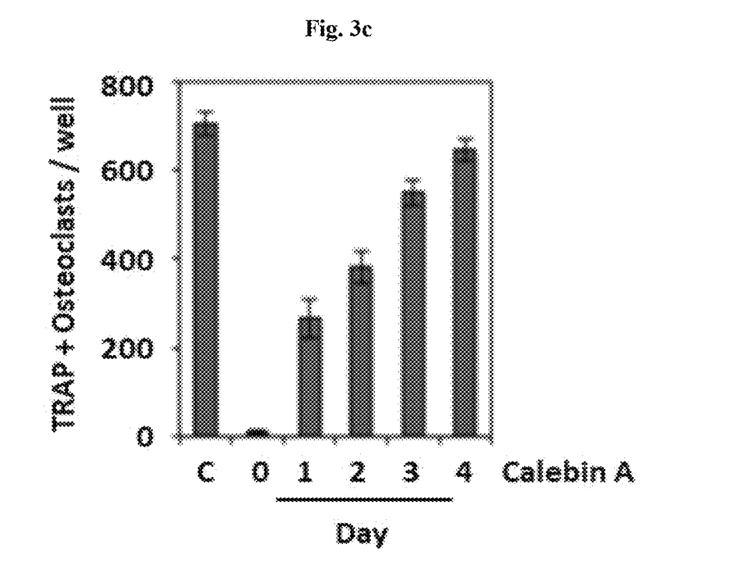
FIG. 3c shows the multinucleated osteoclasts (≥3 nuclei) count. C stands for cells incubated in medium alone. The values are mean of 3 measurements±SD.

The complete RANKL-induced osteoclast differentiation in RAW 264.7 cells normally takes about 5 days. To determine the point at which calebin A acts in the differentiation pathway, RAW 264.7 cells were treated with RANKL and calebin A was added on 0, $1^{st}$, $2^{nd}$, $3^{rd}$, and $4^{th}$ day. The effects on osteoclast formation were measured on day 5 (FIG. 3a). Microscopic observation (FIG. 3b) and counting of the number of TRAP-positive osteoclasts per well (FIG. 3c) showed that calebin A exposure substantially inhibited osteoclast formation at 1-2 days after RANKL stimulation. However, calebin A no longer prevented osteoclast formation at days 3 and 4 after RANKL exposure, (FIG. 3b and FIG. 3c), indicating that it probably acts at an early step in the osteoclast differentiation pathway.

Calebin A Inhibits Osteoclastogenesis Induced by Tumour Cells

Figure 4A:
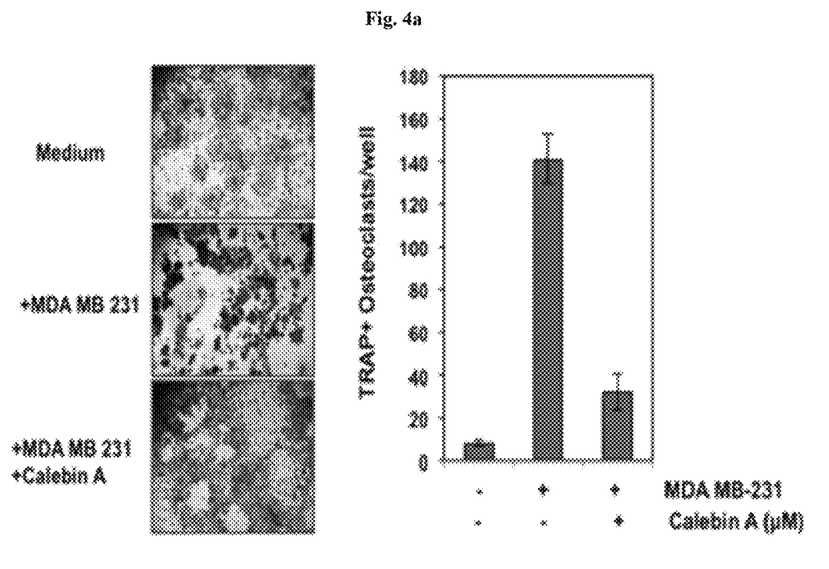
FIG. 4a shows the TRAP expression in stained RAW 264.7 cells ($5 \times 10^3$ cells/mL) incubated in the presence of MDA-MB-231 cells ($1 \times 10^3$ cells/mL), exposed to calebin A (5 mM) for 5 days, and the corresponding multinucleated osteoclast count (Mean±SD).
Figure 4B:
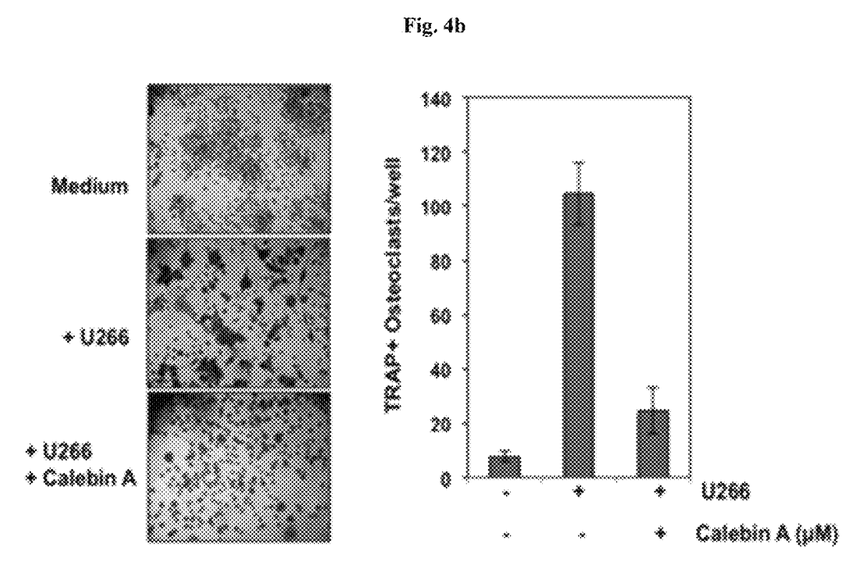
FIG. 4b shows the TRAP expression in stained RAW 264.7 cells ($5 \times 10^3$ cells/mL) incubated in the presence of U266 cells ($1 \times 10^3$ cells/mL, exposed to calebin A (5 mM) for 5 days, and the corresponding multinucleated osteoclast count (Mean±SD).
Figure 4C:
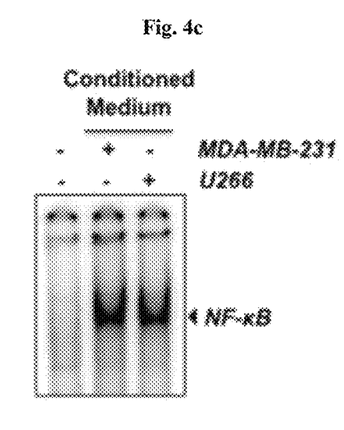
FIG. 4c shows the electrophoretic mobility shift assay (EMSA) for nuclear factor-κB (NFκB) activity in RAW 264.7 cells (1.5×10³ cells per well) incubated in the presence of conditioned medium from MDA-MB-231 or U266 cells for 24 h.

Since increased osteoclastogenesis is commonly linked with breast cancer and multiplemyeloma, whether calebin A modulates osteoclastogenesis induced by these cancer cells in RAW264.7 cells was investigated. RAW264.7 cells and MDAMB-231 breast cancer or U266 multiple myeloma cells were co-incubated and allowed to differentiate for 5 days. It was observed that MDA-MB-231 cells induced differentiation of RAW264.7 cells into osteoclasts and calebin A inhibited this differentiation (FIG. 4a). A similar pattern was observed for U266 cells (FIG. 4b) indicating that calebin A suppresses the process of osteoclastogenesis induced by cancer cells. One major mechanism that has been associated with osteoclastogenesis is the NF-κB activation pathway. Therefore, it was investigated whether the conditioned medium from MDA-MB-231 and U266 cells induced NF-κB activation in RAW 264.7 cells. The results revealed that the conditioned medium indeed effectively activated NF-κB (FIG. 4c) in RAW 264.7 cells. These findings indicate that the NF-κB transcription factor is involved in osteoclast differentiation induced by cancer cells. The present study has shown that calebin A inhibits osteoclastogenesis induced by MDA-MB-231 and U266 cells, suggesting that calebin A is an attractive potential agent for the treatment of patients with bone metastasis.

Calebin A Abrogates RANKL-Induced NF-κB Activation

Figure 5A:
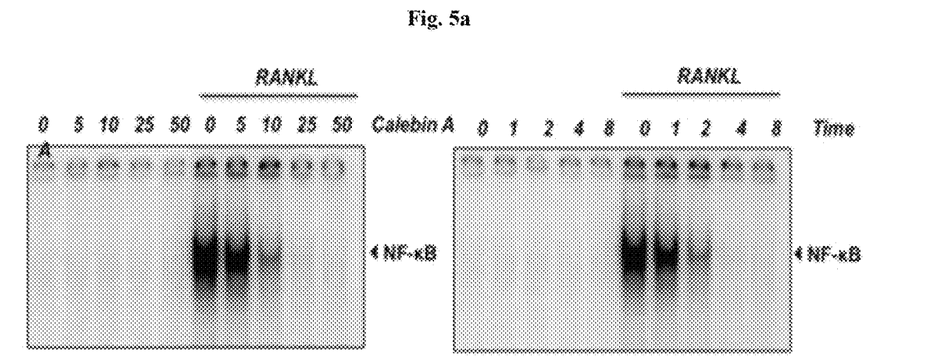
FIG. 5a shows the electrophoretic mobility shift assay (EMSA) for nuclear factor-κB (NFκB) activity in nuclear extracts of RAW 264.7 cells (1.5×10³ cells per well) incubated with 50 mM of calebin A for 8 h and treated with 10 nM RANKL for 30 min.
Figure 5B:
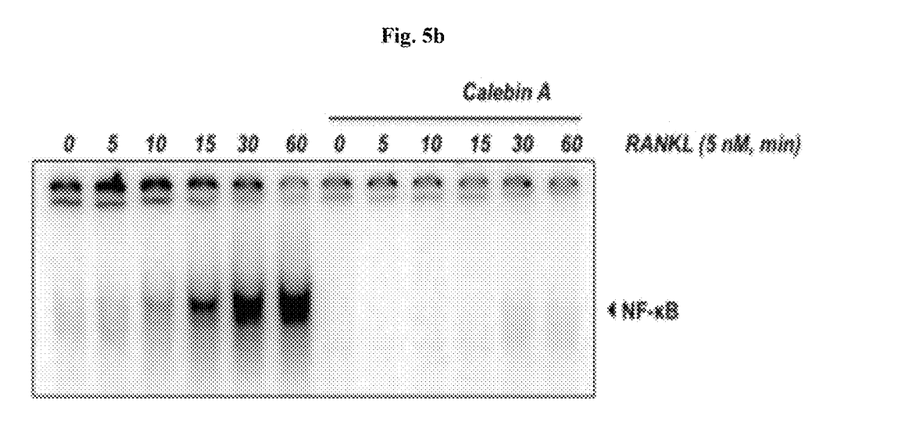
FIG. 5b shows the electrophoretic mobility shift assay (EMSA) for nuclear factor-κB (NFκB) activity in RAW264.7 cells (1.5×10³ cells per well) treated with the indicated concentrations of calebin A for 8 h and treated with 10 nM RANKL for 30 min.

To further examine the modulation of RANKL induced NF-κB activation by calebin A, RAW 264.7 cells were either pretreated with various concentration of calebin A for 8 h (FIG. 5a, left panel) or calebin A (50 mM) for various time periods (FIG. 5a, right panel) and then exposed to RANKL for 30 min (FIG. 5a). NF-κB activation was assayed using EMSA. The results indicated that RANKL activated NF-κB; however, calebin A completely abrogated RANKL-induced NF-κB activation (FIG. 5a). To test the effect of calebin A dose on NF-κB activation in RANKL-exposed cells, RAW 264.7 cells were pretreated with various concentrations of calebin A for 8 h and were then exposed to RANKL for 30 min. It was observed that calebin A completely suppressed NF-κB activation at a dose of 50 mM (FIG. 5b). No effect on the activation of NF-κB was observed when the cells were treated with 50 mM calebin A but without RANKL for 8 h.

Calebin A Inhibits RANKL-Induced IκBα Phosphorylation and Degradation

Figure 5C:
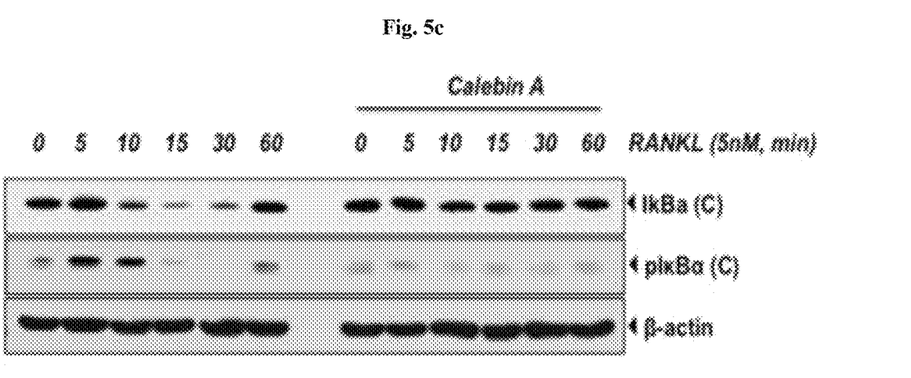
FIG. 5c shows the representative image of a western blot assay for IκBα degradation and phosphorylation in the cytoplasmic extracts of RAW 264.7 cells (1.5×10³ cells per well) incubated with 50 mM of calebin A for 8 h and then treated with 10 nM RANKL for the indicated times (min). β-actin was used as a loading control.

Because nuclear translocation of NF-κB requires the proteolytic degradation of IκBα, it was examined whether calebin A's suppression of NF-κB was caused by inhibition of IκBα degradation. Western blotting was used to assay cytoplasmic IκBα degradation after RANKL stimulation at a range of time intervals (FIG. 5c). RANKL induced IκBα degradation in untreated control cells within 10 min, but IκBα levels returned to normal within 60 min. In contrast, cells pretreated with calebin A exhibited complete inhibition of IκBα degradation (FIG. 5c).

Figure 5D:
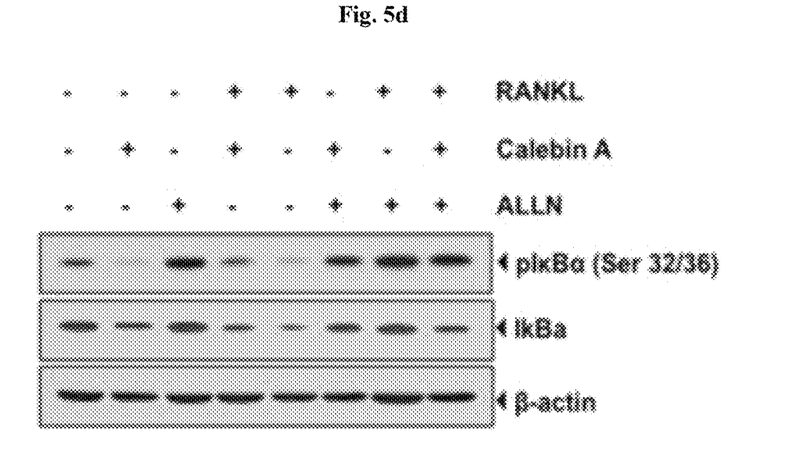
FIG. 5d shows the representative image of a western blot assay for phospho-IκκBα expression in the cytoplasmic extracts of RAW 264.7 cells (1.5×10³ cells per well) incubated with 50 mM of calebin A for 8 h, then incubated with ALLN (50 mg/mL) for 30 min, and finally treated with RANKL (10 nM) for 15 min. The same membrane was reprobed with IκBα and β-actin antibodies.

IκBα phosphorylation is necessary for IκBα degradation. Hence, its was examined whether calebin A affects IκBα phosphorylation. It was observed that RANKL induced IκBα phosphorylation within 5 min. However, phosphorylation was completely inhibited by calebin A pretreatment. The effect of calebin A on IκBα phosphorylation was also investigated by using the proteasome inhibitor N-acetyl-leucyl-leucyl-norleucinal (ALLN), which prevents RANKL-induced IκBα degradation (FIG. 5d). Western blot analysis indicated that co-treatment with RANKL and ALLN induced phosphorylation of IκBα at serines 32 and 36 in RAW264.7 cells. calebin A pretreatment inhibited the induction of phosphorylation. calebin A alone did not induce phosphorylation of IκBα (FIG. 5d). The phosphorylation, ubiquitination, and proteasome-mediated degradation of IκBα in response to RANKL is a rapid process. These results indicate that calebin A inhibits RANKL-induced NF-κB activation through suppression of IκBα degradation and phosphorylation.

Inhibition of Osteoclastogenesis by Calebin A is NF-κB-Specific

Figure 5E:
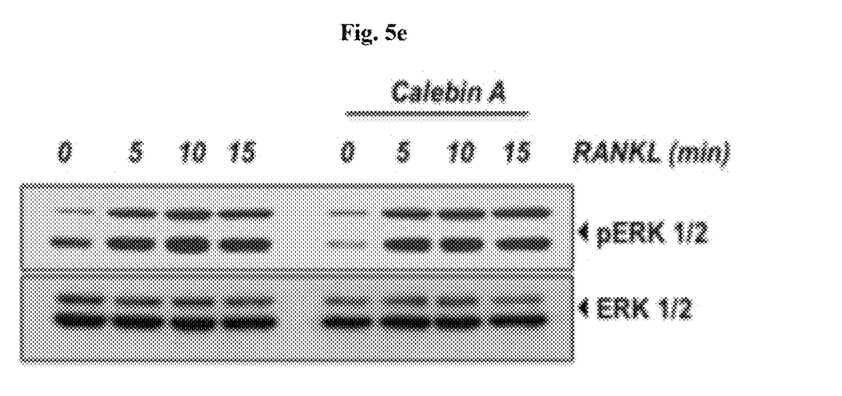
FIG. 5e shows the representative image of a western blot assay for phospho-extracellular signal-related kinase (p-ERK) expression in the whole cell extracts of RAW 264.7 cells (1.5×10³ cells per well) pre-incubated with calebin A for 8 h and then exposed to RANKL (10 nM) for the indicated times. ERK 1/2 was used as a loading control.

Because RANKL-induced osteoclastogenesis is triggered by 2 main signalling pathways, namely, the NF-κB and mitogen activated protein kinase (MAPK) pathways, it was observed whether calebin A pretreatment also affects the MAPK pathway. The effect of calebin A on ERK1/2 activation was examined. RANKL induced ERK1/2 phosphorylation in osteoclast precursor RAW 264.7 cells (FIG. 5e). However, pretreatment of cells with calebin A did not inhibit the RANKL-induced activation of ERK phosphorylation, indicating calebin A-induced inhibition of osteoclastogenesis is not mediated through MAPK pathway.

Inhibition of NF-κB Abrogates Osteoclastogenesis

Figure 6A:
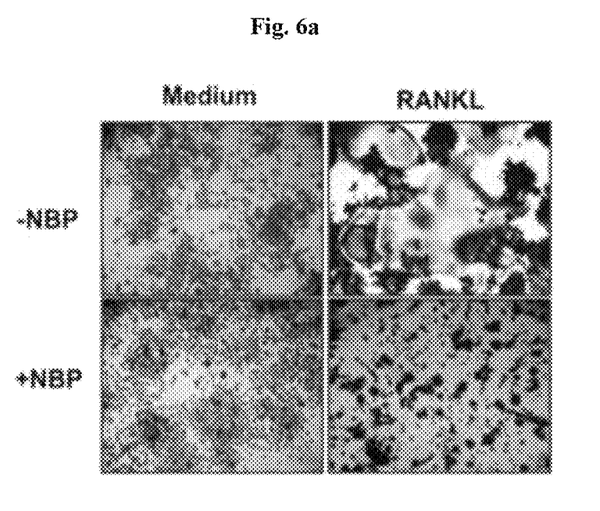
FIG. 6a shows the TRAP expression in stained RAW 264.7 cells (5×10³ cells/mL) pretreated with 100 mM of NEMO-binding domain peptide (NBP) for 2 h and incubated with RANKL (5 nM) for 5 days. Original magnification—100×.
Figure 6B:
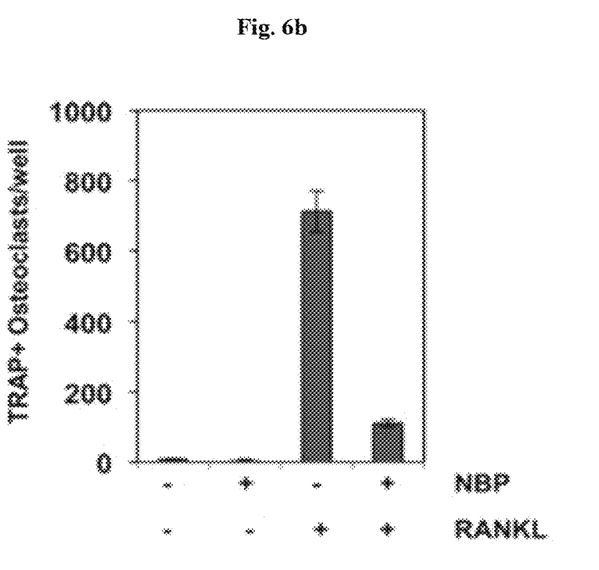
FIG. 6b shows the multinucleated osteoclast (≥3 nuclei) count. The values are mean of 3 measurements±SD.
Figure 6C:
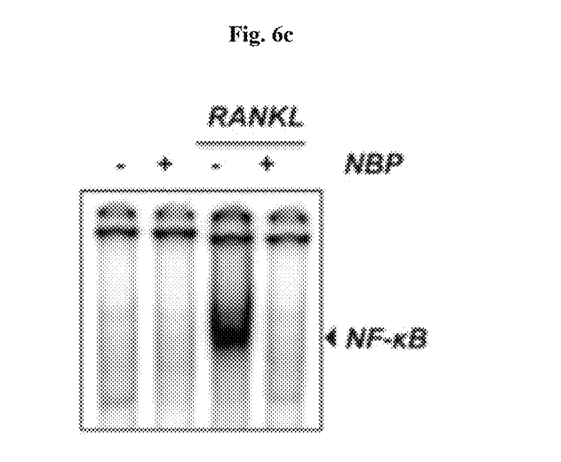
FIG. 6c shows the electrophoretic mobility shift assay (EMSA) for nuclear factor-κB (NFκB) activity in RAW 264.7 cells (1.5×10³ cells per well) incubated with 100 mM of NBP for 2 h and with 10 nM RANKL for 30 min.

It was further examined whether RANKL-induced osteoclastogenesis is caused by the activation of NF-κB using a specific inhibitor of the regulatory subunit of the IKK complex, which is also known as NF-κB essential modulator (NEMO). NEMO binding peptide (NBP blocks the activation of NF-κB). To determine the effect of NBP on RANKL-induced osteoclastogenesis, RAW264.7 cells were pretreated with 100 mM NBP for 2 h and then with RANKL for 5 days. The results showed that RANKL induced osteoclastogenesis and that NBP inhibited it (FIG. 6a and FIG. 6b). Furthermore, it was observed that nuclear extracts from RAW 264.7 cells treated with 100 mM NBP for 2 h and then with RANKL for 30 min completely inhibited NF-κB activation (FIG. 6c). These results confirm that NF-κB activation was responsible for osteoclast differentiation in RAW 264.7 cells and that inhibition of NF-κB with either calebin A or NBP prevented osteoclastogenesis.

Figure 6D:
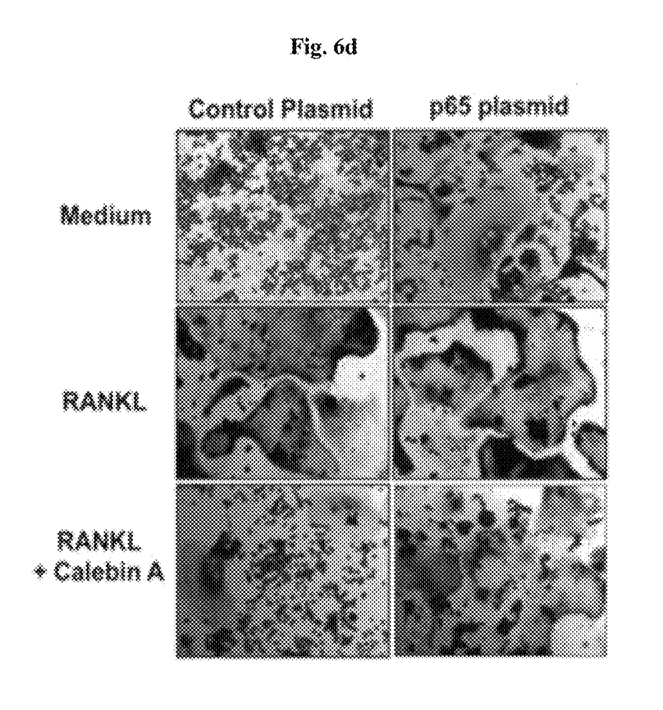
FIG. 6d shows the overexpression of NFκB/p65 reduced inhibitory effects of calebin A on RANKL-induced osteoclastogenesis. RAW 264.7 cells (5×10³ cells/well) were first transfected with control and p65 plasmids. After 24 h cells were treated with 5 mM of calebin A and 5 nM of RANKL for 5 days and then stained to show TRAP expression. Original magnification—100×.

Over Expression of NF-κB/p65 Abolishes Osteoclastogenesis Inhibitory Effects of Calebin A To determine whether calebin A inhibits RANKL-induced osteoclatogenesis mediated through NF-κB activation, p65 was over expressed in cells and then the effect of calebin A on RANKL-induced osteoclatogenesis was studied. Calebin A was observed to minimally inhibited RANKL induced osteoclastogenesis in p65 transfected RAW 264.7 cells, however it almost completely inhibited in cells transfected with control plasmid (FIG. 6d). This result indicates that p65 plays a role in RANKL induced osteoclastogenesis and thus inhibition of NF-κB/p65 by calebin A inhibits osteoclastogenesis.

Calebin A Abrogates M-CSF-Induced Osteoclast Differentiation Markers

Figure 7A:
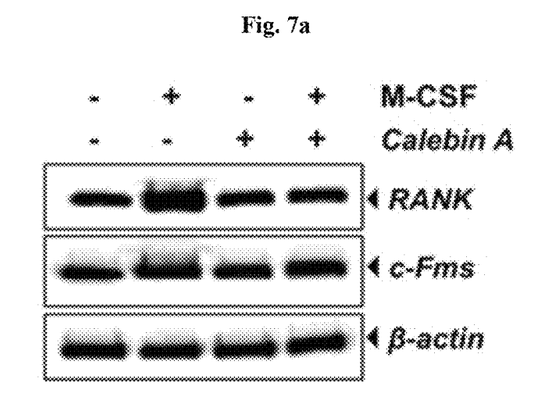
FIG. 7a shows the immunoblotting image for RANK and M-CSF expression in cell lysates of RAW 264.7 cells (1.5×10³ cells per well), incubated with 50 mM of calebin A for 8 h and treated with 20 ng/mL M-CSF for 24 h. β-actin was used as a loading control.

Further to examine the possible role of calebin A in the regulation of osteoclast differentiation in early stage, the RAW 264.7 cells were pre-treated with calebin A and induced by M-CSF for 24 h. Expression of RANK was upregulated by M-CSF and calebin A was observed to downmodulate M-CSF-induced expression of RANK (FIG. 7a). There was no significant variation in c-Fms-expression treated by M-CSF as well as calebin A. Thus, it can be concluded that calebin A inhibits M-CSF-induced RANK expression.

Figure 7B:
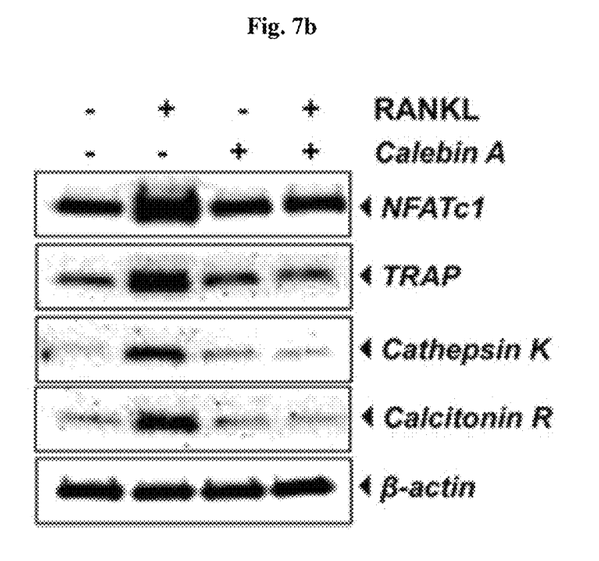
FIG. 7b shows the western blot assay for the expression of for different osteoclastogenesis-related genes in RAW 264.7 cells (1.5×10³ cells per well) incubated with 50 mM of calebin A for 8 h and treated with 10 nM RANKL for 24 h. β-actin was used as a loading control.

Calebin A Inhibits RANKL-Induced NFATc1 and Other Osteoclastogenesis-Related Marker Gene Expression NFATc1 plays a major role in the regulation of osteoclastogenesis. Hence, the effect of calebin A on RANKL-induced NFATc1 expression was investigated. The results indicated that NFATc1 expression was upregulated when exposed to RANKL, and calebin A pretreatment abolished the RANKL-induced NFATc1 expression (FIG. 7b). Basically, activation and nuclear translocation of NFATc1 and osteoclast differentiation are mediated by the expression of large number of marker genes, including TRAP, cathepsin K and calcitonin R, regulated by NFATc1. These genes are activated by the RANKL-mediated signalling pathway. Therefore, the effect of calebin A on the expression of RANKL-induced osteoclastogenesis related marker genes, were also examined. It was observed that RANKL induced the expression of TRAP, cathepsin K and calcitonin R. However, no effect of calebin A alone has been noticed in the expression of these marker proteins (FIG. 7b). These results indicate that calebin A inhibits the RANKL-induced NFATc1, TRAP, cathepsin K and calcitonin R expression.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of inhibiting osteoclastogenesis in mammals, said method comprising steps of bringing into contact mammalian osteoclast progenitor cells with an effective concentration of calebin A to bring about effect of inhibiting differentiation of said progenitor cells into osteoclasts.

2. The method according to claim 1, wherein said progenitor cell is macrophage.

3. A method of inhibiting gene and protein expression associated with up-regulation of osteoclastogenesis in mammals said method comprising steps of bringing into contact mammalian osteoclast progenitor cells with an effective concentration of calebin A to bring about down-regulation of said gene and protein expression in the mammalian progenitor cells.

4. A method of therapeutic management of osteoporosis induced by osteoclastogenesis in mammals, said method comprising step of administering therapeutically effective amounts of calebin A to mammals in need of said therapeutic management to bring about the effect of osteoclastogenesis inhibition.

5. A method of therapeutically managing mammalian osteoporosis resulting from cancer induced differentiation of osteoclast progenitor cells into osteoclasts, said method comprising step of bringing into contact effective concentration of calebin A, said progenitor cells and said cancer cells to bring about the effect of osteoclastogenesis inhibition.

* * * * *